(12) United States Patent
Cherkez et al.

(10) Patent No.: US 10,954,191 B2
(45) Date of Patent: Mar. 23, 2021

(54) PROCESS FOR THE PREPARATION OF GLYCOPYRROLATE TOSYLATE

(71) Applicant: SOL-GEL TECHNOLOGIES LTD., Ness Ziona (IL)

(72) Inventors: Stephen Cherkez, Caesarea (IL); Veera Reddy Arava, Hyderabad (IN); Madhusudhanarao Rayapureddi, Hyderabad (IN); Venkateswarlu Jasti, Hyderabad (IN)

(73) Assignee: Sol-Gel Technologies Ltd., Ness Ziona (IL)

( * ) Notice: Subject to any disclaimer, the term of this patent is extended or adjusted under 35 U.S.C. 154(b) by 0 days.

(21) Appl. No.: 16/493,391

(22) PCT Filed: Mar. 12, 2018

(86) PCT No.: PCT/IL2018/050285
§ 371 (c)(1),
(2) Date: Sep. 12, 2019

(87) PCT Pub. No.: WO2018/167776
PCT Pub. Date: Sep. 20, 2018

(65) Prior Publication Data
US 2020/0377455 A1    Dec. 3, 2020

Related U.S. Application Data

(60) Provisional application No. 62/470,315, filed on Mar. 12, 2017.

(51) Int. Cl.
*C07D 207/12* (2006.01)

(52) U.S. Cl.
CPC .................. *C07D 207/12* (2013.01)

(58) Field of Classification Search
None
See application file for complete search history.

(56) References Cited

U.S. PATENT DOCUMENTS

| 7,915,303 | B2 | 3/2011 | Baxter |
| 9,006,461 | B2 | 4/2015 | Statler et al. |
| 10,294,201 | B2 * | 5/2019 | Shaw ........................ B01D 9/00 |
| 2013/0211101 | A1 | 8/2013 | Statler et al. |
| 2016/0052879 | A1 | 2/2016 | Shaw et al. |

FOREIGN PATENT DOCUMENTS

WO    WO/2010/115937    10/2010

OTHER PUBLICATIONS

International Search Report for PCT Application No. PCT/IL2018/050285 dated May 21, 2018.

* cited by examiner

*Primary Examiner* — Kamal A Saeed
(74) *Attorney, Agent, or Firm* — Mark S. Cohen; Pearl Cohen Zedek Latzer Baratz LLP

(57) ABSTRACT

The present application provides novel process for the preparation of glycopyrrolate tosylate.

31 Claims, No Drawings

PROCESS FOR THE PREPARATION OF GLYCOPYRROLATE TOSYLATE

CROSS-REFERENCE TO RELATED APPLICATIONS

This application is a National Phase Application of PCT International Application No. PCT/IL2018/050285, International Filing Date Mar. 12, 2018, claiming the benefit of U.S. Provisional Application No. 62/470,315, filed Mar. 12, 2017 which are hereby incorporated by reference.

FIELD OF THE INVENTION

The present application provides novel process for the preparation of glycopyrrolate tosylate.

BACKGROUND OF THE INVENTION

Glycopyrronium tosylate, also known as (1,1-dimethylpyrrolidin-1-ium-3-yl) 2-cyclopentyl-2-hydroxy-2-phenylacetate; 4-methylbenzenesulfonate or glycopyrrolate tosylate, is an anti-muscarinic agent. Other glycopyrrolate salts are used as antiasthmatic or antispasmodic agents administered either intravenously, orally or topically in accordance with the medical indication. Glycopyrronium bromide and glycopyrronium tosylate have been clinically tested for the topical treatment of hyperhidrosis.

Glycopyrronium tosylate has the following chemical structure:

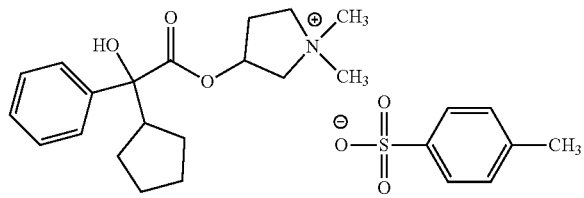 [SMILES: C[N+]1(C)CCC(OC(=O)C(O)(c2ccccc2)C2CCCC2)C1 ; Cc1ccc(S(=O)(=O)[O-])cc1]

Several syntheses of glycopyrrolate tosylate have been disclosed, one of which is the conversion of the glycopyrrolate bromide (commercially available as "glycopyrrolate") into the tosylate. However, these syntheses have been prone to give rise to high levels of by-products, which is highly undesirable and requires further purification processes. Typical syntheses of the glycopyrrolate tosylate have been disclosed in the following patent documents: U.S. Pat. No. 9,006,461, WO 2010/115937 and U.S. Pat. No. 7,915,303.

Acknowledgement of the above references herein is not to be inferred as meaning that these are in any way relevant to the patentability of the presently disclosed subject matter.

There is therefore an unmet need for a process for the preparation of glycopyrrolate tosylate from the glycopyrrolate bromide that affords a pure glycopyrrolate tosylate via an efficient and straightforward process.

SUMMARY OF THE INVENTION

The invention provides a process for the preparation of glycopyrrolate tosylate comprising: (a) preparing a bi-phasic system comprising as reactants a halogen salt of glycopyrrolate and tosylic acid or salt thereof; and (b) reacting the reactants of said system in the presence of at least one phase transfer catalyst; thereby preparing the glycopyrrolate tosylate.

In another aspect the invention provides a process for the preparation of glycopyrrolate tosylate comprising reacting (a) an aqueous solution comprising at least a tosylic acid or salt thereof; and (b) a non-aqueous solution comprising at least a halogen salt of glycopyrrolate, wherein said reaction is performed in the presence of at least one phase transfer catalyst.

The invention further provides a process for the preparation of glycopyrrolate tosylate comprising reacting
  a. an aqueous solution comprising at least a tosylic acid or salt thereof; and
  b. a non-aqueous solution comprising at least a halogen salt of glycopyrrolate; thereby preparing said glycopyrrolate tosylate.

In other embodiments, this invention provides a process for the preparation of glycopyrrolate tosylate comprising:
  a. preparing a bi-phasic system comprising a halogen salt of glycopyrrolate and tosylic acid or a salt thereof; and
  b. reacting said system to prepare said glycopyrrolate tosylate.

DETAILED DESCRIPTION OF THE PRESENT INVENTION

The invention provides a process for the preparation of glycopyrrolate tosylate comprising: (a) preparing a bi-phasic system comprising as reactants a halogen salt of glycopyrrolate and tosylic acid or salt thereof; and (b) reacting the reactants of said system in the presence of at least one phase transfer catalyst; thereby preparing the glycopyrrolate tosylate.

The term "biphasic system" should be understood to encompass a liquid system that has two non-miscible phases, comprising a halogen salt of glycopyrrolate and a tosylic acid or salt thereof.

In some embodiments, the bi-phasic system comprises at least one aqueous solution comprising said tosylic acid or salt thereof. In further embodiments, the bi-phasic system comprises at least one non-aqueous solution comprising said halogen salt of glycopyrrolate.

In another aspect the invention provides a process for the preparation of glycopyrrolate tosylate comprising reacting (a) an aqueous solution comprising at least a tosylic acid or salt thereof; and (b) a non-aqueous solution comprising at least a halogen salt of glycopyrrolate, wherein the reaction is performed in the presence of at least one phase transfer catalyst.

The term "phase transfer catalyst" (PTC) should be understood to encompass any heterogeneous catalyst that facilitates the migration of a reactant from one phase into another phase where reaction occurs. PTC typically functions similarly to a detergent facilitating the solubility of salts from the aqueous phase into the second non-miscible phase (for example the organic phase). Phase-transfer catalysis allows for the acceleration of the reaction upon the addition of the phase-transfer catalyst.

The term " . . . reacting the reactant of said system in the presence of at least one phase transfer catalyst" should be understood to relate to the fact the reaction between the reactants of the system brought together in the two separate none-miscible phases transpires upon the presence of the PTC in said system.

The term "reaction is performed in the presence of at least one phase transfer catalyst" should be understood to relate to the fact the reaction between the aqueous solution comprising at least a tosylic acid or salt thereof and the non-aqueous solution comprising at least a halogen salt of glycopyrrolate transpires upon the presence of the PTC in said system.

In some embodiments the PTC is added to one phase of the bi-phasic system prior to mixing (in some embodiments the PTC is added to the aqueous phase, in another embodiment the PTC is added to the non-aqueous phase).

In some embodiments, the PTC is added to the bi-phasic system after mixing of the two none-miscible phases.

In other embodiments, the at least one aqueous solution further comprises said at least one phase transfer catalyst. In further embodiments, the at least one non-aqueous solution further comprises said at least one phase transfer catalyst.

In some embodiments, said at least one phase transfer catalyst is selected from tetra-butyl ammonium bromide (TBAB), N-Methyl-N,N,N-trioctylammonium chloride (aliquat-336), 1,4,7,10,13,16-hexaoxacyclooctadecane (18-Crown-6), hexadecyl-trimethylammonium bromide, tetrabutylammonium iodide (TBAI), and any combination thereof.

In further embodiments, the at least one phase transfer catalyst is added to said prior to or during the reaction.

In some other embodiments, the non-aqueous solution comprises at least one of cyclohexane, toluene, methylene chloride, chloroform, and any combinations thereof. In some other embodiments, the non-aqueous solution comprises cyclohexane, toluene, methylene chloride, chloroform, carbon tetrachloride, chlorobenzene, 1,2 dichloroethane, hexane, heptane, cyclopentane, benzene, xylene, ethyl acetate or any combination thereof.

In other embodiments, the halogen salt of glycopyrrolate is a bromide salt. In another embodiment, the halogen salt of the glycopyrrolate is a chloride, iodide or fluoride salt.

In another embodiment the molar ratio between the tosylic acid and the glycopyrrolate is about 1:1. In another embodiment the molar ratio between the PTC and the tosylic acid is between 0.5 to 5% mol %. In a preferred embodiment the molar ratio between the PTC and the tosylic acid is between 2 to 3% mol %.

In further embodiments, the aqueous solution comprises at least a tosylic acid or salt thereof. Non limiting examples of tosylic acid salts include: ammonium; quaternary ammonium; alkali metals such as lithium, sodium, potassium, cesium; alkaline metals such as calcium, magnesium, aluminum, zinc, barium; organic amines such as aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines or ureas.

In other embodiments, the aqueous solution further comprises a base. In other embodiments the base is an alkali base, NaOH, KOH, Ba(OH)$_2$, CsOH, Ca(OH)$_2$, LiOH or any combination thereof. Each represents a separate embodiment of this invention. In other embodiment, the molar ratio between the base and the tosylic acid is about 1:1.

In another embodiment, the aqueous solution contains at least one salt selected from potassium carbonate, sodium chloride, potassium chloride and mixtures thereof.

In some embodiments said process of the invention further comprises a step of at least one purification step of the glycopyrrolate tosylate product. In some said purification step is a recrystallization process, thus producing a solid glycopyrrolate tosylate product.

In some embodiments, a process of the invention produces a glycopyrrolate tosylate product (prior to any purification or recrystallization processes) having less than 2% halide content. In some embodiments, a process of the invention produces a glycopyrrolate tosylate product (prior to any purification or recrystallization processes) having less than 1% halide content. In some embodiments, a process of the invention produces a glycopyrrolate tosylate product (prior to any purification or recrystallization processes) having less than 0.5% halide content. In some embodiments, a process of the invention produces a glycopyrrolate tosylate product (prior to any purification or recrystallization processes) having between 0.1% to 2% halide content. In some other embodiments, the halide content relates to the glycopyrrolate bromide content at the end reaction step prior to any purification or recrystallization process. It should be noted that having less than 2% halide content at the end of the reaction step allows for only a single purification process for achieving the glycopyrrolate tosylate product in the purification levels needed for pharmaceutical processing, i.e. 0.01% to 0.5% of glycopyrrolate bromide.

In a further aspect the invention provides a process for the preparation of glycopyrrolate tosylate comprising: (a) preparing a bi-phasic system comprising a halogen salt of glycopyrrolate, tosylic acid or salt thereof; and two immiscible solvents; (b) adding at least one phase transfer catalyst to one of the immiscible solvents or to the bi-phasic system; and (c) mixing the resulting bi-phasic reaction mixture until the completion of the anion exchange process; (d) separating the crude glycopyrrolate tosylate product; and (e) purifying the crude product to obtain pure glycopyrrolate tosylate.

In some embodiment the glycopyrrolate tosylate is obtained in the non-aqueous phase. Following the reaction between glycopyrrolate and the tosylic acid or salt thereof, the two phases are being separated and the glycopyrrolate is obtained from the non-aqueous phase.

In another one of its aspects the invention provides a process for the preparation of glycopyrrolate tosylate comprising reacting (a) an aqueous solution comprising at least a tosylic acid or salt thereof; and (b) a non-aqueous solution comprising at least a halogen salt of glycopyrrolate; thereby preparing said glycopyrrolate tosylate.

In another aspect the invention provides a process for the preparation of glycopyrrolate tosylate comprising (a) preparing a bi-phasic system comprising a halogen salt of glycopyrrolate with tosylic acid or salt thereof; and (b) reacting said system to prepare said glycopyrrolate tosylate.

In one embodiment, the process for the preparation of glycopyrrolate tosylate does not include PTC. In another embodiment, such process yields glycopyrrolate halide with less than about 5% (prior to any purification or recrystallization processes). In another embodiment, such process yields glycopyrrolate halide with about 3 to 5% (prior to any purification or recrystallization processes). In some embodiments, following additional purification or recrystallization processes, glycopyrrolate tosylate is obtained with less than 1% of glycopyrrolate halide. In some embodiments, following additional purification or recrystallization processes, glycopyrrolate tosylate is obtained with between 0.01 to 0.5% of glycopyrrolate halide.

In some embodiments, said reaction disclosed in the aspects of the invention is performed for at least 24 h. In other embodiments, said reaction disclosed in the aspects of the invention is performed for at least 32 h.

The invention will now be illustrated by the following non-limiting Examples.

EXAMPLES

Example 1. Preparation of Glycopyrrolate Tosylate in Dichloromethane Using Tetrabutylammonium Bromide as a Phase Transfer Catalyst To a stirred solution of water 30 mL, sodium hydroxide 1.014 g (25.35 mmol) was added, followed by addition of p-toluene sulfonic acid 4.823 g (25.35 mmol) at 30° C., then glycopyrrolate bromide 10 g (25.1 mmol) and dichloromethane 100 mL and a phase transfer catalyst tetrabutylammonium bromide 0.2 g (0.62 mmol) were added and the clear bi-phasic solution was stirred at 25-30° C. for 24 h. The organic layer was separated, and the aqueous layer was extracted with dichloromethane 25 mL×2. The combined dichloromethane layer was treated with 0.5 g carbon, and then filtered through micron filter. The organic solvent dichloromethane was distilled under reduced pressure and cyclohexane 40 mL was added to the syrupy liquid to precipitate the product. The mixture was stirred for 1 h at 25° C. to complete the precipitation. The product was filtered and washed with 20 mL cyclohexane to afford the crude product (9.0 g, 17.73 mmol, 70.6% yield) and bromide percentage 1.55%. The crude product was further purified by dissolving in 36 mL water at 50° C. and isolating by cooling to 5° C. to obtain 7.5 g (14.77 mmol, 58.8% yield), of white crystalline solid with a bromide content of 0.11%. Further crystallization was performed by dissolving in dichloromethane (75 mL) and removing the solvent by evaporation under reduced pressure and triturating with 30 mL cyclohexane, filtering and washing with 10 mL cyclohexane. The solid was dried at 30° C. affording 6.75 g (13.2 mmol, 53% yield), essentially free of bromide, water content 3.62%, and complying with the specifications.

Example 2. Preparation of Glycopyrrolate Tosylate without Using a Phase Transfer Catalyst To a stirred solution of water 60 mL, sodium hydroxide 2.03 g (50.70 mmol) was added, followed by the addition of p-toluene sulfonic acid 9.65 g (50.70 mmol) at 30° C., then glycopyrrolate bromide 20 g (50.2 mmol) and dichloromethane 200 mL were added and the clear bi-phasic solution was stirred at 25-30° C. for 32 h. The organic layer was separated and the aqueous layer was extracted with dichloromethane 50 mL×2. The combined dichloromethane layer was treated with 1.0 g carbon and filtered through a micron filter. The solvent dichloromethane was distilled under reduced pressure and cyclohexane 80 mL was added to the syrupy liquid to precipitate the product. The mixture was stirred for 1 h at 25° C. to complete the precipitation. The product was filtered and washed with 40 mL cyclohexane to afford the crude product (19.0 g, 37.42 mmol, 75.46% yield), bromide percentage 4.65% and water content 3.37%. The crude product was further crystallized as shown in Example 1 affording 14.02 gm (27.6 mmol, 55% yield), and complying with the specifications, i.e. 0.01% to 0.5% of glycopyrrolate bromide.

Example 3. Preparation of Glycopyrrolate Tosylate in a Mixture of Dichloromethane and Cyclohexane Using Tetrabutylammonium Bromide as a Phase Transfer Catalyst To a stirred solution of water 30 mL sodium hydroxide 1.01 g (25.35 mmol) was added followed by the addition of p-toluene sulfonic acid 4.82 g (25.35 mmol) at 30° C., then glycopyrrolate bromide 10 g (25.1 mmol), cyclohexane 100 mL, dichloromethane 2.0 mL, tetrabutylammonium bromide 0.2 g (0.62 mmol), were added and the clear bi-phasic solution was stirred at 25-30° C. for 24 h. The precipitated p was cooled to 5° C., stirred for 1 h, and filtered and washed with cyclohexane 20 mL to get the crude product 10.0 g (19.71 mmol, 78.74% yield), and bromide percentage 1.12%. The crude product was further purified with water as described in Example 1 herein above, to afford 9.0 g (70.64% yield), bromide—0.08%, water content 3.97%, and complying with the specifications.

Example 4. Preparation of Glycopyrrolate Tosylate in a Mixture of Dichloromethane and Cyclohexane Using Tetrabutylammonium Bromide as a Phase Transfer Catalyst To a stirred solution of water 40 mL sodium hydroxide 1.01 g (25.35 mmol) was added followed by the addition of p-toluene sulfonic acid 4.82 g (25.35 mmol) at 30° C., then glycopyrrolate bromide 10 g (25.1 mmol), cyclohexane 100 mL, dichloromethane 2.0 mL, and tetrabutyl ammonium bromide 0.2 g (0.62 mmol), were added and the clear bi-phasic solution was stirred at 25-30° C. for 24 h. The precipitated product was cooled to 5° C., stirred for 1 h, filtered and washed with cyclohexane 20 mL to get the crude product 10.0 g (19.71 mmol, 78.74%), and bromide content of 0.36%. The product was further purified with water as described in Example 1 hereinabove affording 9.0 g (70.64% yield), bromide content of 0.08%, water content 3.78%, and was complying with the specifications.

Example 5. Preparation of Glycopyrrolate Tosylate in a Mixture of Dichloromethane and Cyclohexane Using 18-Crown-6 as a Phase Transfer Catalyst To a stirred solution of water (20 mL) sodium hydroxide 0.5 g (12.5 mmol) was added followed by the addition of p-toluene sulfonic acid 2.42 g (12.72 mmol) at 30° C., then glycopyrrolate bromide 5.0 g (12.55 mmol), cyclohexane 50 mL, dichloromethane 1.0 mL, and 18-Crown-6 0.1 g (0.378 mmol), were added and the clear bi-phasic solution was stirred at 25-30° C. for 24 h. The precipitated product was cooled to 5° C., stirred for 1 h, filtered and washed with 10 mL cyclohexane to get the crude product 5.42 g (10.67 mmol, 85% yield), and bromide content of 0.48%. The crude product was further purified with water as described in Example 1 hereinabove affording 4.0 g (69.67% yield), and essentially free of bromide. The product was further purified in dichloromethane affording 3.51 g (6.91 mmol, 55.27% yield), bromide content of 0.17%, water content 3.06%, and complying with the specifications.

Example 6. Preparation of Glycopyrrolate Tosylate in a Mixture of Dichloromethane and Cyclohexane Using Hexadecyl Trimethyl Ammonium Bromide as a Phase Transfer Catalyst To a stirred solution of water 100 mL sodium hydroxide 2.53 g (63.3 mmol) was added followed by the addition of p-toluene sulfonic acid 12.1 g (63.6 mmol) at 30° C., then glycopyrrolate bromide 25.0 g (63.3 mmol), cyclohexane 250 mL, dichloromethane 5.0 mL, and hexadecyl trimethyl ammonium bromide 0.5 g (1.37 mmol), were added and the clear bi-phasic solution was stirred at 25-30° C. for 24 h. The precipitated material was cooled to 5° C., stirred for 1 h and filtered and washed with cyclohexane 50 mL to get the crude product 23.4 g (46.09 mmol) 73.7%, bromide percentage was 1.16%, it was further purified with water as described in Example 1 herein above weight 22.0 g 70.8% yield, bromide percentage absent, water content 3.61%, and was complied with the specifications.

Example 7. Preparation of Glycopyrrolate Tosylate in a Mixture of Dichloromethane and Cyclohexane Using Aliquat-336 as a Phase Transfer Catalyst To a stirred solution of water 100 mL sodium hydroxide 2.53 g (63.3 mmol) was added followed by the addition of p-toluene sulfonic acid 12.1 g (63.6 mmol) at 30° C., then glycopyrrolate bromide 25.0 g (63.3 mmol), cyclohexane 250 mL, dichloromethane 5.0 mL, and Aliquat-336 0.5 g (1.237 mmol), were added and the clear bi-phasic solution was stirred at 25-30° C. for 24 h. The precipitated product was cooled to 5° C., stirred for 1 h, filtered and washed with cyclohexane 50 mL to get the crude product 24.6 g (48.45 mmol, 77.48%), and bromide content of 1.03%. The crude product was further purified with water as described in Example 1 hereinabove affording 22.5 g (72.6% yield) and bromide content of 0.04%, water content of 3.82%, and complying with the specifications.

The invention claimed is:

1. A process for the preparation of glycopyrrolate tosylate comprising
    (a) preparing a bi-phasic system comprising a halogen salt of glycopyrrolate and tosylic acid or a salt thereof; and
    (b) reacting said system in the presence of at least one phase transfer catalyst;
thereby preparing said glycopyrrolate tosylate.

2. A process for the preparation of glycopyrrolate tosylate comprising reacting
    (a) an aqueous solution comprising at least a tosylic acid or salt thereof; and
    (b) a non-aqueous solution comprising at least a halogen salt of glycopyrrolate;
wherein said reaction is performed in the presence of at least one phase transfer catalyst, thereby preparing said glycopyrrolate tosylate.

3. A process according to claim 1, wherein said bi-phasic system comprises at least one aqueous solution comprising said tosylic acid or salt thereof.

4. A process according to claim 1, wherein said bi-phasic system comprises at least one non-aqueous solution comprising said halogen salt of glycopyrrolate.

5. A process according to claim 2, wherein said at least one aqueous solution further comprises said at least one phase transfer catalyst.

6. A process according to claim 2, wherein said at least one non-aqueous solution further comprises said at least one phase transfer catalyst.

7. A process according to claim 4, wherein said non-aqueous solution comprises at least one of cyclohexane, toluene, methylene chloride, chloroform and any combinations thereof.

8. A process according to claim 2, wherein said non-aqueous solution comprises at least one of cyclohexane, toluene, methylene chloride, chloroform, and any combinations thereof.

9. A process according to claim 1, wherein said halogen salt of glycopyrrolate is a bromide salt.

10. A process according to claim 1, wherein said at least one phase transfer catalyst is selected from tetra-butyl ammonium bromide (TBAB), N-Methyl-N,N,N-trioctylammonium chloride (aliquat-336), 1,4,7,10,13,16-hexaoxacyclooctadecane (18-Crown-6), hexadecyltrimethylammonium bromide, tetrabutylammonium iodide (TBAI), and any combination thereof.

11. A process according to claim 2, wherein said aqueous solution further comprises a base.

12. A process according to claim 1, wherein said at least one phase transfer catalyst is added to said biphasic system prior to or during the reaction.

13. A process according to claim 1, wherein the glycopyrrolate tosylate product comprises less than 2% halide content.

14. A process according to claim 1, wherein the glycopyrrolate tosylate product comprises less than 1% halide content.

15. A process according to claim 1, wherein the glycopyrrolate tosylate product comprises less than 0.5% halide content.

16. A process for the preparation of glycopyrrolate tosylate comprising reacting
    (a) an aqueous solution comprising at least a tosylic acid or salt thereof; and
    (b) a non-aqueous solution comprising at least a halogen salt of glycopyrrolate;
thereby preparing said glycopyrrolate tosylate.

17. A process for the preparation of glycopyrrolate tosylate comprising
    (a) preparing a bi-phasic system comprising a halogen salt of glycopyrrolate and tosylic acid or a salt thereof; and
    (b) reacting said system to prepare said glycopyrrolate tosylate.

18. A process according to claim 16, wherein said reaction is performed for at least 24 h.

19. A process according to claim 16, wherein said reaction is performed for at least 32 h.

20. A process according to claim 16, wherein said halogen salt of glycopyrrolate is a bromide salt.

21. A process according to claim 3, wherein said at least one aqueous solution further comprises said at least one phase transfer catalyst.

22. A process according to claim 4, wherein said at least one non-aqueous solution further comprises said at least one phase transfer catalyst.

23. A process according to claim 2, wherein said halogen salt of glycopyrrolate is a bromide salt.

24. A process according to claim 2, wherein said at least one phase transfer catalyst is selected from tetra-butyl ammonium bromide (TBAB), N-Methyl-N,N,N-trioctylammonium chloride (aliquat-336), 1,4,7,10,13,16-hexaoxacyclooctadecane (18-Crown-6), hexadecyltrimethylammonium bromide, tetrabutylammonium iodide (TBAI), and any combination thereof.

25. A process according to claim 3, wherein said aqueous solution further comprises a base.

26. A process according to claim 2, wherein said at least one phase transfer catalyst is added to said biphasic system prior to or during the reaction.

27. A process according to claim 2, wherein the glycopyrrolate tosylate product comprises less than 2% halide content.

28. A process according to claim 2, wherein the glycopyrrolate tosylate product comprises less than 0.5% halide content.

29. A process according to claim 17, wherein said reaction is performed for at least 24 h.

30. A process according to claim 17, wherein said reaction is performed for at least 32 h.

31. A process according to claim 17, wherein said halogen salt of glycopyrrolate is a bromide salt.

\* \* \* \* \*